US006872394B1

(12) United States Patent
Bohach

(10) Patent No.: US 6,872,394 B1
(45) Date of Patent: Mar. 29, 2005

(54) NON-TOXIC IMMUNE STIMULATING ENTEROTOXIN COMPOSITIONS

(75) Inventor: Gregory I. Bohach, Moscow, ID (US)

(73) Assignee: Idaho Research Foundation, Inc., Moscow, ID (US)

( * ) Notice: Subject to any disclaimer, the term of this patent is extended or adjusted under 35 U.S.C. 154(b) by 0 days.

(21) Appl. No.: 09/555,115

(22) PCT Filed: Dec. 1, 1998

(86) PCT No.: PCT/US98/25107

§ 371 (c)(1),
(2), (4) Date: Aug. 1, 2000

(87) PCT Pub. No.: WO99/27889

PCT Pub. Date: Jun. 10, 1999

Related U.S. Application Data

(60) Provisional application No. 60/067,357, filed on Dec. 2, 1997.

(51) Int. Cl.[7] .................... A61K 39/00; A61K 39/38; C07K 1/00; C07K 14/00
(52) U.S. Cl. .................. 424/184.1; 424/185.1; 424/190.1; 424/234.1; 424/237.1; 424/243.1; 424/244.1; 530/300; 530/350
(58) Field of Search .......................... 424/184.1, 185.1, 424/190.1, 234.1, 237.1, 243.1, 244.1; 530/300, 350

(56) References Cited

U.S. PATENT DOCUMENTS 5,885,780 A * 3/1999 Olivera et al.

FOREIGN PATENT DOCUMENTS

| WO | WO 91/10680 | 7/1991 |
| WO | WO 93/24136 | 12/1993 |
| WO | WO 97/36932 | 10/1997 |

OTHER PUBLICATIONS

Alakhov, V. et al., "Identification of Functionally Active Fragments of Staphylococcal Enterotoxin B", *Eur. J. Biochem.*, vol. 209, pp. 823–828 (Feb. 1992).

Bayles, K. et al., "Genetic and Molecular Analyses of the Gene Encoding Staphylococcal Enterotoxin D", *Journal of Bacteriology*, vol. 171, No. 9, pp. 4799–4806 (Sep. 1989).

Binek, M. et al., "Localisation of the Mitogenic Epitope of Staphylococcal Enterotoxin B", *J. Med. Microbiol.*, vol. 36, pp. 156–163 (1992).

Bohach, G. et al., "Expression of Staphylococcal Enterotoxin C1 in *Escherichia coli*", *Infection and Immunity*, vol. 55, No. 2, pp. 428–432 (Feb. 1987).

Bonventre, P. et al., "A Mutation at Histidine Residue 135 of Toxic Shock Syndrome Toxin Yields an Immunogenic Protein with Minimal Toxicity", *Infection and Immunity*, vol. 63, No. 2, pp. 509–515 (Feb. 1995).

Couch, J. et al., "Cloning and Nucleotide Sequence of the Type E Staphylococcal Enterotoxin Gene", *Journal of Bacteriology*, vol. 170, No. 7, pp. 2954–2960 (Jul. 1988).

Hovde, C. et al., "Investigation of the Role of the Disulphide Bond in the Activity and Structure of Staphylococcal Enterotoxin C1", *Molecular Microbiology*, vol. 13, No. 5, pp. 897–909 (1994).

Liu, C.T. et al., "Effect of Staphylococcal Enterotoxin B on Cardiorenal Functions in Rhesus Macaques", American Journal of *Veterinary Research*, vol. 39, No. 2, pp. 279–286 (Feb. 1978).

Liu, C.T. et al., "Effect of Staphylococcal Enterotoxin B on Cardiorenal Functions and Survival in X–Irradiated Rhesus Macaques", American Journal of *Veterinary Research*, vol. 39, No. 7, pp. 1213–1217 (Jul. 1978).

Leung, D. et al., "Bacterial Superantigens Induce T Cell Expression of the Skin–selective Homing Receptor, the Cutaneous Lymphocyte–associated Antigen, via Stimulation of Interleukin 12 Production", *Journal of Experimental Medicine*, vol. 181, No. 2, pp. 747–753, (Feb. 1995).

Nishi, J. et al., "B Cell Epitope Mapping of the Bacterial Superantigen Staphylococcal Enterotoxin B", *The American Association of Immunologists*©, pp. 247–254 (1997).

Reda, K. et al., "Molecular Characterization and Phylogenetic Distribution of the Streptococcal Superantigen Gene (ssa) from *Streptococcus pyogenes*", *Infection and Immunity*, vol. 62, No. 5, pp. 1867–1874, (May 1994).

* cited by examiner

*Primary Examiner*—Mark Navarro
(74) *Attorney, Agent, or Firm*—Merchant & Gould P.C.

(57) ABSTRACT

Pyrogenic toxins, such as *staphylococcal* enterotoxins, modified in the disulfide loop region are provided. The modified toxins retain useful biological properties but have substantially reduced toxicity compared to the corresponding unmodified native toxin. The native pyrogenic toxins are typically modified by deletions within the disulfide loop region to produce modified enterotoxins having 100-fold or greater decrease in toxicity.

12 Claims, No Drawings

NON-TOXIC IMMUNE STIMULATING ENTEROTOXIN COMPOSITIONS

This application is a national phase filing of International Patent Application PCT/US98/25107 filed Dec. 1, 1998, which claims benefit of U.S. Provisional Application No. 60/067,357 filed on Dec. 2, 1997.

GOVERNMENT SUPPORT

This invention was funded in part by the United States Department of Health under NIH grant R11A128401. The United States Government has certain rights in the invention.

BACKGROUND OF THE INVENTION

A group of biological agents termed superantigens has been described based on their ability to stimulate monocytes and unprimed $CD4^+$ (MHC Class II restricted) and $CD8^+$ (MHC Class I restricted) T-cells. Included with the designation of superantigens are the enterotoxins of *Staphylococcus aureus*.

The enterotoxins of *Staphylococcus aureus* form a group of serologically distinct proteins, originally designated A, B, $C_1$, $C_2$, $C_3$, D, E, G, and H. Subsequently, a number of variants have been described. These proteins and toxic shock syndrome proteins were originally recognized as the causative agents of *staphylococcal* food poisoning. Ingestion of preformed enterotoxin in contaminated food leads to the rapid development (within two to six hours) of symptoms of vomiting and diarrhea that are characteristic of *staphylococcal* food poisoning. Toxic shock syndrome toxin-1, TSST- 1, a distantly related protein also produced by *S. aureus*, is classically responsible for the toxic shock syndrome, although other *staphylococcal* enterotoxins may result in the syndrome due to the induction of cytokines.

Other agents which have been identified as superantigens include for example, the *staphylococcal* exfoliative toxins, A and B; the mammary tumor virus superantigen; rabies virus nucleocapsid protein; pyrogenic exotoxins A, B, C from *S. pyrogens*; and the *Mycoplasma arthritides* mitogen. Additional biological agents which have been demonstrated to have superantigen properties include the human immunodeficiency virus (HIV), gp120 and peptides from HIV, mouse mammary tumor virus and feline immunodeficiency virus. A Leishmania peptide antigen has also been disclosed as a superantigen.

Superantigens, unlike conventional antigens, do not require processing in-vivo. In general, superantigens have two binding regions, one of which interacts with the Class II major histocompatibility complex (MHC) on the antigen presenting cell and the other which interacts with the Vβ variable region of the T-cell receptor on CD4 and/or CD8 cells. Various enterotoxins bind to one or more of the different Vβ receptor epitopes. In contrast to conventional antigens, superantigens do not occupy the T-cells receptor cleft but are felt to bind to an external region thus explaining the ability to activate a broad population of T-cells.

Enterotoxins produced by *Staphylococcus aureus* include a group of related proteins of about 20 to 30 Kd. The complete amino acid composition of a number of *staphylococcal* enterotoxins and *streptococcal* pyrogenic exotoxin has been reported (see e.g., PCT Patent Appl. No. WO 93/24136.)

*Staphylococcal* enterotoxins ("SEs") were initially classified on the basis of their antigenic properties into groups A, B, C1, C2, C3, D, and E. Subsequent relatedness was based on peptide and DNA sequence data. Among the *staphylococcal* enterotoxins, groups B and C are closely related and groups A, D, and E are closely related in amino acid sequence. SEC1, SEC2, and SEC3 and related isolates share approximately 95% sequence similarity. Table 1 shows the alignment of the predicted sequences of the eight known SEC variants following cleavage of the signal peptide. The N-terminus of each of the mature proteins was verified by amino acid sequencing. Amino acid positions that contain residues that are not conserved among all SEC are indicated by asterisks. SEB and SEC are approximately 45–50% homologous. In contrast, non-enterotoxin superantigens, TSST-1 and *Streptococcal* Pyrogenic Enterotoxin C (SPEC) share only approximately 20% primary sequence homology to SEC. Despite these differences, the tertiary structure of the various enterotoxins show nearly identical folds.

The *staphylococcal* enterotoxins A, B, $C_1$, $C_2$, $C_3$, D, E, G and H share a common structural feature of a disulfide bond not present in other enterotoxins. Table 2 shows the position of the disulfide bond in a number of enterotoxins. Data in reference to the active sites of the enterotoxin molecule in relationship to biological activity, MHC binding, and TCR binding has been obtained. Sequence data demonstrate a high degree of similarity in four regions of the enterotoxins (See Table 3). The peptides implicated in potential receptor binding correspond to regions 1 and 3 which form a groove in the molecule. Amino acid residues within and adjacent to the $\alpha_3$ cavity of SEC3 have been shown to relate to T-cell activation.

TABLE 2

LOCATION OF DISULFIDE LOOP IN STAPHYLOCOCCUS ENTEROTOXINS

| ENTEROTOXIN | AMINO ACID RESIDUES | AMINO ACID SEQUENCE OF DISULFIDE LOOP | |
|---|---|---|---|
| SEA | 96–106 | 96?CAGGTPNKTAC | (SEQ. ID. NO:9) |
| SEB | 93–114 | 93?CYFSKKTNDINSHQTPKRKTC | (SEQ. ID. NO:10) |
| SEC1 | 93–110 | 93?CYFSSKDNVGKVTGGKTC | (SEQ. ID. NO:11) |
| SEC2 | 93–110 | 93?CYFSSKDNVGKVTGGKTC | (SEQ. ID. NO:12) |
| SEC3 FRI 913 | 93–110 | 93?CYFSSKDNVGKVTGGKTC | (SEQ. ID. NO:13) |
| SEC3 FRI 909 | 93–110 | 93?CYFSSKDNVGKVTSGKTC | (SEQ. ID. NO:14) |
| SEC 4446 | 93–110 | 93?CYFSSKDNVGKVTGGKTC | (SEQ. ID. NO:15) |
| SEC-Bovine | 93–110 | 93?CYFSSKDNVGKVTGGKTC | (SEQ. ID. NO:16) |
| SEC-Ovine | 93–110 | 93?CCFSSKDNVGKVTGGKTC | (SEQ. ID. NO:17) |

The *staphylococcal* enterotoxins are potent activators of T-cells, resulting in proliferation and the generation of cytotoxic T-cells. SEA is a potent T-cell mitogen eliciting strong polyclonal activation at concentrations of $10^{-13}$ to $10^{-10}$ molar in human systems.

The *staphylococcal* enterotoxins, aside from the acute gastroenteritis and toxic shock syndrome associated with them, have been shown to have a variety of other beneficial biological effects. The biological effects of these agents and the toxic shock syndrome are due in part to the ability of *staphylococcal* enterotoxins to induce cytokines. Various cytokines described include IL-1, IL-2, and tumor necrosis factor ("TNF"). More recently SEB and toxic shock syndrome toxin ("TSST-1") have been shown to induce interleukin-12, an inducer of cell mediated immunity, in human peripheral blood mononuclear cells. (See Leung et al., *J Exp Med*, 181:747 (1995)). The antitumor activity of treating cancer in rabbits utilizing 40 to 60 µg/kg of a *staphylococcal* enterotoxin has been disclosed in PCT Patent Appl. Nos. WO 91/10680 and WO 93/24136.

Exposure to enterotoxin either in-vitro or in-vivo leads to depletion of T-cells having the appropriate Vβ receptor through programmed cell death in some strains of mice, specifically Balb/c and CBA/2. Cell death can be prevented by high doses of retinol or RU-38486. Programmed cell death has not been observed upon exposure of human cells to enterotoxins.

Although the systemic lethal toxicity of enterotoxins has been related to their ability to induce cytokines, particularly IL-1, IL-2 and gamma interferon, lethal toxicity also appears to be related to a synergistic activity with endogenous endotoxins and the ability of the liver to detoxify endotoxins. Although a number of animals have been utilized to evaluate lethality, the accepted model is the continous infusion over a period of time, usually 4 days, in rabbits. The direct toxic dose varies among various species. The 50% lethal dose of TSST-1 is approximately 50 µg/kg for Balb/c mice. Piglets, although showing clinical manifestations of toxic shock syndrome, tolerate doses of 100 µg/kg of TSST-1. TSST-ovine is known to be non-toxic at doses of 200 µg in rabbits.

In Dutch belted rabbits, intramuscular injection of 50 mg/kg of *staphylococcal* enterotoxin B caused death. Intravenous injection at 0.5 to 1.0 mg/kg of enterotoxin A or B in rhesus macaques results in hypotension and death (Liu C. T., et al *Amer J Vet Res* 39:279 and 1213, 1978).

In contrast to other species, man is extremely sensitive to enterotoxins. One (1) mg of TSST-1, approximately 15 nanogram/kg, can be lethal for man. Therefore, the recommended doses currently proposed in the art for treating man are unacceptable. There is a need, therefore, for mutant *staphylococcal* enterotoxins which are non-toxic at anticipated doses for man while still retaining desirable biological activity.

Several studies of *staphylococcal* enterotoxin have identified a number of biologically active modified or mutant enterotoxins with reduced toxicity. Carboxymethylation of SEB results in a loss of gastrointestinal toxicity but not mitogenic activity. Studies with the TSST-1 have demonstrated the active site to be between amino acids residue 115 and 141. Point mutation of site 135 from histidine to alanine results in a loss of mitogenic activity and toxicity (See Bonventre P. F., et al. *Infect Immun* 63:509(1995)). Studies with the *staphylococcal* enterotoxin SEC1 demonstrated that the disulfide bond between residue 93 and 110 is not required for activity (See Hovde et al., *Mol Microbiol* 13:897 (1994)). Studies of the molecular binding region of *staphylococcal* enterotoxin B using overlapping peptides demonstrated peptide 124 to 154 inhibited SEB induced mitogenic activity.

Based on the known biological activities of the toxic native enterotoxins, it is desirable to create mutants which are at least 1000-fold or more less toxic compared to native enterotoxins and retain biological activity. Recent studies have demonstrated that mutant enterotoxins can be produced which retain certain biological activities and which may be significantly less lethal as determined in rabbits. A mutant of the TSST-1 enterotoxin which differs in amino acid 136 and is non-lethal at ten times the lethal dose of the native toxin (in rabbits), but retains biological activity has been disclosed. A number of mutants of SEC1, unable to form a disulfide bond, have been reported to be ten times less toxic than the native toxin while retaining biological activity. (See e.g., Hovde et al., *Molec Microbiol* 13:897 (1994)).

SUMMARY OF THE INVENTION

The present invention relates to modified versions of disulfide loop-containing bacterial pyrogenic toxins. The modified pyrogenic toxins retain useful biological properties but have substantially reduced toxicity (e.g., toxicity reduced by at least about 10-fold) compared to the corresponding unmodified native toxin. Selected deletions within the disulfide loop region can produce modified toxins having a 100-fold or greater decrease in toxicity. The toxicity of the modified toxin can be measured based on a variety of parameters, including emetic response inducing activity, fever inducing activity, and lethality (as measured by $LD_{50}$ in Dutch Belted rabbits).

Examples of the present modified toxins include disulfide loop region deletion mutants of native toxins derived from *Staphylococcus aureus* or *Streptococcus pyrogenes*. Suitable native disulfide loop-containing toxins which may be modified according to the present invention include Type A, B, C, D and E *staphylococcal* enterotoxins as well as *streptococcal* pyrogenic enterotoxin A ("SPEA") and *streptococcal* superantigen ("SSA") produced by *S. pyrogenes*.

The pyrogenic toxins constitute a family of exotoxins produced by species of gram positive *cocci*, such as *Staphylococcus* and *Streptococcus*. The pyrogenic toxins are characterized by shared ability to induce fever, enhance host susceptibility to endotoxin shock, and induce T cell proliferation through action as superantigens. Examples of pyrogenic toxins include TSST-1, *staphylococcal* enterotoxins (SEs), and *streptococcal* pyrogenic exotoxins (SPEs). In addition to the activities listed above, some pyrogenic toxins have additional activities that are not shared by all pyrogenic toxins. For example, the *staphylococcal* enterotoxins induce emesis and diarrhea when ingested. Structurally, the pyrogenic toxins have varying degrees of relatedness at the amino acid and nucleotide sequence levels. A number of the pyrogenic toxins include a disulfide loop as a structural feature. The *staphylococcal* enterotoxins have a disulfide loop, as do some others in this family. Examples of other pyrogenic toxins that have a disulfide loop are the *streptococcal* superantigen ("SSA") and *streptococcal* pyrogenic exotoxin A ("SPEA").

The pyrogenic toxins have varying degrees of relatedness which provides the basis for separating some of them informally into subgroups. One subgroup includes *staphylococcal* type B and C enterotoxins ("SEB" and "SEC"), as well as SPEA and SSA. These toxins share between about 49% to greater than 95% amino acid sequence homology (Reda et al, *Infect. Immun.,* 62:1 867–1874: (1994)). Another subgroup of related pyrogenic toxins include *staphylococcal* type A and E enterotoxins (SEA and SEE) which are 83% homologous to each other (Couch et al, *J. Bacteriol.,* 70:2954–2060 (1988), less so but significantly to SED (Bayles et al., *J. Bacteriol.,* 171:4799–4806 (1989)). The amino acid sequences of this second subgroup is more distantly related to SEB, SEC, SPEA, and SSA. Examples of pyrogenic toxins having disulfide bonds are present in both of these two subgroups. TSST-1 and *streptococcal* pyrogenic exotoxins B and C (SPEB and SPEC) are examples of a third subgroup of less related toxins. Although toxins from this third subgroup may share some conserved regions (see table 3) with toxins from the other subgroups, there is little overall sequence homology between toxins in the third subgroup and the pyrogenic toxins in the other two subgroups. Neither TSST-1, SPEB nor SPEC includes a disulfide loop.

The disulfide loop region of a native pyrogenic toxin, such as a native *staphylococcal* enterotoxin, is generally modified through deletion of a number of amino acid residues within the loop. The modification typically includes deletion of amino acid residues within the disulfide loop region and may include one or more substitutions and/or additions to the remaining loop residues. After modification, the disulfide loop region typically contains no more than about 10 and, preferably, no more than about 6 amino acids residues. In another embodiment of the invention, a modified pyrogenic toxin is formed from a native pyrogenic toxin modified by deletion of at least 40% of the amino acid residues within the disulfide loop region, e.g., by deletion of 8 or more amino acid residues from the disulfide loop region of a native type C *staphylococcal* enterotoxin.

The present invention is also directed to isolated nucleic acids which include a nucleotide sequence encoding a modified pyrogenic toxin.

DETAILED DESCRIPTION OF THE INVENTION

The current invention relates to modified versions of pyrogenic toxins, such as *staphylococcal* enterotoxins produced by modifications which include deletions in the disulfide bond region. The present invention describes the feasibility of obtaining mutant pyrogenic toxins which retain biological activity but demonstrate significantly lower toxicity at doses well in excess of the normal lethal dose and levels anticipated for human therapeutic use.

The modified pyrogenic toxins are derived from a native pyrogenic toxin having a disulfide loop. The terms "disulfide loop" and "disulfide loop region" are used interchangeably herein. As employed in this application, these terms refer to the sequence of about 10 to about 30 amino acid residues forming a loop defined by a disulfide bond in a native pyrogenic toxin. The term "disulfide loop region" also refers to the corresponding portion of the sequence of a modified pyrogenic toxin which has been produced by deletion, substitution or addition of one or more amino acid residues of the disulfide loop of a native pyrogenic toxin. The disulfide loop region is defined to begin with the N-terminal Cys residue and end with the C-terminal Cys residue of the loop, e.g., amino acid residues 93–110 of *staphylococcal* enterotoxin C1. As used herein, the positions of the disulfide loop region for a given native pyrogenic toxin are numbered beginning with the N-terminal cyteine residue in the loop, e.g., position 93 of type B or C *staphylococcal* enterotoxins is also referred to herein as position 1 of the disulfide loop region.

The modification of the disulfide loop typically includes deletion of at least about 40% of the amino acid residues within the disulfide loop. For example, this generally results in the deletion of at least about 8 amino acid residues from the disulfide loop region of an SEC. Examples of native *staphylococcal* enterotoxin which can be modified to form the present low toxicity toxins include type A, B, C, D, E, G, and H *staphylococcal* enterotoxins. Type C *staphylococcal* enterotoxins such as *staphylococcal* enterotoxin C1, *staphylococcal* enterotoxin C2, *staphylococcal* enterotoxin C2, *staphylococcal* enterotoxin C-MNCopeland, *staphylococcal* enterotoxin C-4446, *staphylococcal* enterotoxin C-bovine (GenBank Accession No. L13374), *staphylococcal* enterotoxin C-canine (GenBank Accession No. V19526) and *staphylococcal* enterotoxin C-ovine (GenBank Accession No. L13379) are particularly suitable enterotoxins for modification by deletion of a portion of the disulfide loop region to form a *staphylococcal* enterotoxin with decreased toxicity.

The modified disulfide loop region generally contains no more than about 10 amino acid residues and, preferably no more than 6 amino acid residues. For example, a type C *staphylococcal* enterotoxin, such as *staphylococcal* enterotoxin C1, can be modified to delete amino acid residues 98–106 (residues 6–14 of the disulfide loop) to form a modified *staphylococcal* enterotoxin having substantially reduced toxicity. An even greater reduction in toxicity is produced by deleting amino acid residues 95–106 (disulfide loop residues 3–14) of *staphylococcal* enterotoxin C1. Both of these mutants, despite having substantially reduced toxicity, are biologically active as evidenced by their ability to stimulate the uptake of thymidine by human peripheral blood mononuclear cells.

In addition to deletion of a number of the disulfide loop residues, substitution of a cysteine residue for the residue at position 2 of disulfide loop can contribute to a decrease in the toxicity of a pyrogenic toxin such as a type C *staphylococcal* enterotoxin. In a preferred embodiment, *staphylococcal* enterotoxin C1 can be modified so that in addition to deletion of a substantial portion of the residues in the loop region, the amino acid residue at position 2 of the loop, Tyr-94, is replaced by a cysteine.

Other examples of preferred embodiments of the invention include modified *staphylococcal* enterotoxins having no more than 10 amino acid residues and, preferably, no more than 6 amino acid residues in the disulfide loop region. Particularly preferred examples include *staphylococcal* enterotoxins with no more than about 9 amino acid residues which include the sequence Cys-Gly-Lys-Thr. One example of such a mutant is *staphylococcal* enterotoxin C1 modified to have the disulfide loop region sequence Cys-Cys-Gly-Lys-Thr-Cys.

The methods of this invention employed in preparing mutant enterotoxins, and their screening, analysis, and purification are known in the art and described herein. Site directed mutagenesis can be carried out by initially cloning the SEC1structural gene SEC$_{MNDON}$ on a 1.4 Kb MindITI-BamH1 restriction fragment. A unique SphI restriction site (5'-GCATGC-3') can be introduced into SEC$_{MNDON}$ in the region coding for the disulfide loop at nucleotides 301–306 (5'-GTAGGT-3') using a commercially available kit (Altered Sites in vitro Mutagenesis System, Promega). Potential mutants may be screened by Sph1 digestion and confirmed by nucleic acid sequence analysis.

Select SEC$_{MNDON}$ deletion mutants were cloned into an *E. coli* cell line using pMIN164 an *E. coli-S. aureus* shuttle vector. To facilitate protein purification, recombinant plasmids from *E. coli* RR1 transformants were transformed into *S. aureus* RN4220 by standard protoplast transformation techniques. Plasmids containing cloned toxin genes were maintained in *S. aureus* RN4220 under erythromycin (50 mg/ml) selection. For purification of native and mutant derivatives of the toxin recombinants, *S. aureus* RN4220 cultures were grown in dialyzable beef heart media supplemented with 1% glucose buffer (330 mM glucose; 475 mM NaHCO$_3$; 680 mM NaCl; 137 mM Na$_2$HPO$_4$.H$_2$O; 28 mM L-glutamine) and erythromycin (50 mg/ml) followed by ethanol precipitation.

Purification of ethanol precipitated proteins was accomplished by preparative flat bed isoelectric focusing (IEF). Following the IEF run, proteins in select fractions were pooled, dialyzed to remove the amphylotes and then visually assessed by sodium dodecyl sulfate polyacrylamide gel electrophoresis (SDS-PAGE).

The toxicity and biological activity of the mutants was evaluated using standard methods known to those skilled in the art as described below. The emetic activity of SEC1, and the SEC1 mutant toxins was determined by a modification of the standard monkey feeding assay using young adult pigtail monkeys (*M. nemestrina*). The animals were manually restrained while the toxin was administered through a nasogastric tube (Infant feeding tube; Becton Dickinson, Rutherford, N.J.). Toxins were screened for retention of emetic activity at a dose of 10 μg/Kg which is approximately 100 times the minimal emetic dose for SEC1. Non-emetic toxins were tested for residual emetic activity at a high dose of 250 μg/kg.

The mitogenic capacities of mutant toxins were compared to that of SEC1 native toxin by using human peripheral blood mononuclear cells (PMBC) in a standard 4-day assay. Solutions of native and mutant toxin were added in triplicate to PBMC cell suspensions, 1×10$^6$ cells/ml, in 96-well tissue culture plates. This mixture of cells and toxin was then incubated at 37° C. under atmospheric conditions of 6% CO$_2$ for 72 hours. [$^3$H]-thymidine (New Research Products, Boston, Mass.) at a concentration of 1 μCi/25 μl in a complete RPMI medium was added to each well and allowed to incubate under the same conditions for an additional 18–24 hours. After incubation, radiolabeled cellular nucleic acids were harvested onto glass fiber filters (Skatron, Sterling, Va.) using a semi-automatic cell harvester (Skatron). Lymphocyte proliferation was quantitated by measuring incorporation of [$^3$H]-thymidine into cellular DNA using a liquid scintillation counter (TRI-CARB 1500 Liquid Scintillation Center, Packard, Rockville, Md.).

The ability of a *staphylococcal* enterotoxin to induce a fever response and enhance susceptibility of lethal endotoxic shock can be determined in vivo using a standard rabbit model (Bohach et al., *Infect. Immun.*, 55, 428 (1987)). Following conditioning in a test rack and having baseline body temperature recorded, adult New Zealand White rabbits can be initially intravenously injected with a native or mutant toxin at a concentration of 10 μg/kg in sterile physiological saline. Sterile saline and purified SEC1 toxin are typically used as negative and positive controls respectively. Following toxin injection, rabbit body temperature is generally monitored rectally every hour for four hours. Four hours after initial treatment, an intravenous injection of lipopolysaccharide ("LPS") from *Salmonella typhimurium* (Difco Laboratories, Detroit, Mich.) is administered intravenously at a concentration of 10 μg/Kg in sterile saline. Animals are then observed for signs of shock and mortality for 48 hours after LPS injection.

Cytokine induction may be determined by utilizing isolated mononuclear cells from heparinized venous blood. Briefly, heparinized venous blood is obtained and layered onto lymphocyte separation medium. The tubes are spun and the mononuclear layer is harvested, washed in PBS, resuspended in RPMI containing 10% FCS and adjusted to 1×10$^6$ cells per ml. Aliquots of 100 μl are typically placed into 96-well microtiter plates. The enterotoxins were added in 100 μl to a final concentration of 1 ng/ml. Following incubation at 37° C. for 48–72 hours, the supernatant was harvested can be assayed for cytokines using commercially available kits from R&D Systems Minneapolis, Minn.

The invention will be further described by reference to the following examples. These examples illustrate but do not limit the scope of the invention that has been set forth herein. Variation within the concepts of the invention will be apparent.

EXAMPLE 1

The SEC1 structural gene, SEC$_{MNDON}$, was previously cloned on a 1.4 Kb HindIII-BamH1 restriction fragment (Bohach et al., *Infect. Immun.*, 55, 428 (1987)). A unique SphI restriction site (5'-GCATGC-3') was introduced into SEC$_{MNDON}$ in the region coding for the disulfide loop at nucleotides 301–306 (5'-GTAGGT-3') using a commercially available kit (Altered Sites in vitro Mutagenesis System, Promega). Potential mutants were screened by Sph1 digestion and confirmed by nucleic acid sequence analysis.

EXAMPLE 2

The unique Sph1 site was used to linearize the SEC$_{MNDON}$ gene so that bi-directional deletions could be generated using Bal-31 exonuclease (Boehringer Mannheim, Indianapolis, Ind.). Bal-31 generated deletion mutant plasmids were ligated and transformed into *E. coli* TG1. Transformants growing on LB-AMP (125 μg/ml) with in-frame stable deletions were detected by screening with SEC1 specific rabbit antisera in immunodiffusion and analyzed by nucleic acid sequence analysis. Sequencing reactions were done using Sequenase Version 2.0, a commercially available kit (U.S. Biochemical Corp., Cleveland, Ohio).

Three deletion mutants were chosen for detailed analysis based on the size and location of the deletions in the loop region of the toxin; SEC1-4AA, SCE1-9AA, and SEC1-12AA. Following purification, each of the disulfide loop mutant toxins could be distinguished from wild type SEC1on the basis of size when analyzed by sodium dodecyl sulfate polyacrylamide gel electrophoresis.

The nucleic acid and amino acid sequences for SEC1 and three deletion mutants are shown in Table 4.

EXAMPLE 3

Mutant Toxin Purification

Select SEC$_{MNDON}$ deletion mutants were cloned into *E. coli* RR1 using pMIN164, an *E. coli-S. aureus* shuttle vector. To facilitate protein purification, recombinant plasmids from *E. coli* RR1 transformants were transformed into *S. aureus* RN4220 by standard protoplast transformation techniques. Plasmids containing cloned toxin genes were maintained in *S. aureus* RN4220 under erythromycin (50 μg/ml) selection. For purification of the recombinantly produced native and mutant derivatives of the toxin, *S. aureus* RN4220 cultures were grown in dialyzable beef heart media supplemented with 1% glucose buffer (330 mM glucose; 475 mM NaHCO$_3$; 680 mM NaCl; 137 mM Na$_2$HPO$_4$.H$_2$O; 28 mM L-glutamine) and erythromycin (50 µg/ml) followed by ethanol precipitation.

Purification of ethanol precipitated proteins was accomplished by preparative flat bed isoelectric focusing ("IEF"). Following the IEF run, proteins in select fractions were pooled, dialyzed to remove the ampholytes and then visually assessed by sodium dodecyl sulfate polyacrylamide gel electrophoresis (SDS-PAGE).

EXAMPLE 4

Emesis Assay

Assays of the emetic activity of SEC1 and the modified SEC1 toxins were conducted using a modification of the standard monkey feeding assay using young adult pigtail monkeys (*M. nemestrina*). The animals were manually restrained while the toxin was administered through a nasogastric tube (Infant feeding tube; Becton Dickinson, Rutherford, N.J.). Toxins were screened for retention of emetic activity at a dose of 10 µg/Kg which is approximately 100 times the minimal emetic dose for SEC1. Non-emetic toxins were tested for residual emetic activity at a high dose of 250 mg/Kg.

It has been previously shown that the minimal emetic dose of wild type SEC1 for *M. nemestrina* was 0.1 µg/Kg. For initial experiments in which the emetic ability was tested, loop mutant toxins were administered at 10 µg/Kg. This insured an excess of toxin over the wild type SEC1 minimal emetic dose. Following intragastric toxin inhibition, animals were observed for at least 12 hours for an emesis response. SEC1-12AA did not show emesis at the 10 µg/Kg concentration and was subsequently tested for emesis at a higher toxin concentration, 250 µg/Kg. Even at this higher doseage level, the SEC1-12AA loop mutant toxin showed no emetic response (See Table 5).

TABLE 5

| Emetic Response[c] of SEC1 Loop Deletion Mutants | | | | |
|---|---|---|---|---|
| Dose[a] | SEC1 | SEC1-4aa | SEC1-9aa | SEC1-12aa |
| 250 µg/Kg | ND[b] | ND | ND | 0/2 |
| 10 µg/Kg | 2/2 | 2/2 | 2/2 | 0/2 |
| 1 µg/Kg | 2/2 | 2/2 | 0/1 | ND |

[a]µg Toxin/Kg Body Weight
[b]ND = Not Determined
[c]Number animals exhibiting emetic response/Total number of animals

EXAMPLE 5

Pyrogenicity and Enhancement of Lethal Endotoxic Shock

The SEC1 mutant toxin's ability to induce a fever response and enhance susceptibility of lethal endotoxic shock was determined in vivo using a previously described rabbit model. Following 1 hour of conditioning in a test rack and having baseline body temperature recorded, adult New Zealand White rabbits were initially intravenously injected with SEC1 or SEC1 mutant toxin at a concentration of 10 µg/Kg in sterile physiological saline. Sterile saline and purified SEC1 toxin were used as negative and positive controls, respectively. Following toxin injection, rabbit body temperature was monitored rectally every hour for four hours. Four hours after initial treatment an intravenous injection of lipopolysaccharide (LPS) from *Salmonella typhimurium* (Difco Laboratories, Detroit, Mich.) was administered intravenously at a concentration of 10 µg/Kg in sterile saline. Animals were watched for signs of shock and mortality for 48 hours after LPS injection.

Wild type SEC1, administered at both 10 µg/Kg and 1 µg/Kg, showed a typical temperature rise (Table 6) as well as an enhanced susceptibility to endotoxic shock (Table 7).

TABLE 6

Maximum Temperature Rise in °C. in Rabbits Given Noted Amount of Native SEC1, Compound to SEC1-4, SEC1-9, or SEC1-12 Mutant

| | SEC1 | SEC1-4aa | SEC1-9aa | SEC1-12aa |
|---|---|---|---|---|
| 100 µg | ND | ND | ND | 0.6 |
| 10 µg | 1.6 | 1.46 | 0.9 | 0.45 |
| 1 µg | 1.3 | 1 | 0.43 | ND |
| 0.1 µg | 1.05 | 0.65 | ND | ND |
| 0.01 µg | 0.475 | 0.425 | ND | ND |

TABLE 7

Lethality in Dutch Belted Rabbits of Native SEC1 and SEC1 Deletion Mutants

| Dose (µg) | SEC1 | SEC1-4 | SEC1-9 | SEC1-12 |
|---|---|---|---|---|
| 100 | ND | ND | ND | 0/3 |
| 10 | 3/3 | 3/3 | 2/3 | 0/3 |
| 1 | 2/2 | 3/3 | 0/3 | ND |
| 0.1 | 3/3 | 2/3 | ND | ND |
| 0.01 | 1/4 | 0/3 | ND | ND |

SEC1-12AA loop mutant toxin concentration was increased to 100 µg/Kg after test animals showed both reduced pyrogenic effects and no susceptibility to endotoxin shock at the initial dose tested, 10 µg/Kg. Following this log fold increase of the SEC-12AA mutant toxin to 100 µg/Kg it was seen that the mutant toxin induced a slight temperature increase over the initial SEC1-12AA loop mutant toxin concentration tested but was not lethal in the assay.

EXAMPLE 6

Mitogenicity

The mitogenic capacity of mutant toxin was compared to that of SEC1 native toxin by using human peripheral blood mononuclear cells (PMBC) in a standard 4-day assay (Bohach et al., *Infect. Immun.*, 55, 428 (1987)). Human peripheral blood mononuclear cells were isolated from 30 to 60 ml of heparinized blood obtained by venipuncture. The blood was mixed 1:1 with Dulbecco's Phosphate Buffered Saline (PBS) (without Calcium or magnesium) and layered onto Fico/Lite (density 1.079 g/ml, Atlanta Biologicals, Norcross, Ga.) and centrifuged at 400×g for 20 minutes. The interface containing the mononuclear cells was removed and washed 3 times with PBS. After the last wash, the pellet was resuspended in Hank's Balanced Salt solution without calcium or magnesium and layered on Fetal Bovine Serum (Atlanta Biologicals, Norcross, Ga.) and centrifuged at 100×g for 10 minutes to remove the platelets. The cells were washed in Hank's Balanced Salt solution, Cat. No. M1211-

021-LV (Atasca, Ill.). A cell count was done by Trypan Blue exclusion.

Solutions of native and mutant toxins were added in triplicate to PMBC cell suspensions, $1\times10^6$ cells/ml, in 96 well tissue culture plates. This mixture of cells and toxin was then incubated at 37° C. under atmospheric conditions at 6% $C_{O2}$ for 72 hours. [$^3$H]-thymidine (New Research Products, Boston, Mass.) at a concentration of 1 $\mu$Ci/25 $\mu$l in a complete RPMI medium was added to each well and allowed to incubate under the same conditions for an additional 18–24 hours. After incubation, radiolabeled cells were harvested onto glass fiber filters (Skatron, Sterling, Va.) using a semi-automatic cell harvester (Skatron). Lymphocyte proliferation was quantitated by measuring incorporation of [$^3$H]-thymidine into cellular DNA using a liquid scintillation counter (TI-CARB 1500 Liquid Scintillation Counter, Packard, Rockville, Md.).

Using SEC1 wild type toxin as a control it was determined that the SEC1-12AA loop mutant toxin showed mitogenic activity at a reduced effectiveness compared to native SEC1 and the SEC1-4 and SEC1-9 mutants in stimulating PMBC cells (see Table 8).

TABLE 8

SEC1 Loop Mutant Mitogeneicity [$^3$H]-Thymidine Uptake (in CPM) of Enterotoxin Stimulated Human Peripheral Blood Mononuclear Cels

| Dose | SEC1 | SEC1-4AA | SEC1-9AA | SEC1-12AA |
|---|---|---|---|---|
| 0.1 pg | 1918 | 2067 | 1067 | 978 |
| 1 pg | 8533 | 7453 | 2360 | 954 |
| 0.01 ng | 14138 | 15495 | 7682 | 1200 |
| 0.1 ng | 21557 | 23689 | 21481 | 6500 |
| 1 ng | 30329 | 28892 | 28951 | 9400 |
| 0.01 $\mu$g | 33089 | 31640 | 23333 | 2700 |

All publications and patent applications in this specification are indicative of the level of ordinary skill in the art to which this invention pertains and are hereby incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention.

TABLE 1

Amino Acid Sequence of Selected Staphylococcal Enterotoxins

| | | | |
|---|---|---|---|
| | | 40 | |
| | | * * * * * * * *? * * * ** | |
| SEC1 (SEQ. ID. NO:1) | 1 | ESQPDPTPDELHKASKFTGLMENMKVLYDDHYVSATKVKSVDKFLAHDLIYNISDKKLKNYDKVKTELLNEGLAKKYKDE | 80 |
| SEC2 (SEQ. ID. NO:2) | 1 | ESQPDPTPDELHKSSEFTGTMGNMKYLYDDHYVSATKVMSVDKFLAHDLIYNISDKKLKNYDKVKTELLNEDLAKKYKDE | 80 |
| SEC3-FR1913 (SEQ. ID. NO:3) | 1 | ESQPDPMPDDLHKSSEFTGTMGNMKYLYDDHYVSATKVKSVDKFLAHDLIYNISDKKLKNYDKVKTELLNEDLAKKYKDE | 80 |
| SEC3-FR1909 (SEQ. ID. NO:4) | 1 | ESQPDPMPDDLHKSSEFTGTMGNMKYLYDDHYVSATKVKSVDKFLAHDLIYNINDKKLNNYDKVKTELLNEDLANKYKDE | 80 |
| SEC-MNCopeland (SEQ. ID. NO:5) | 1 | ESQPDPTPDELHKSSEFTGTMGNMKYLYDDHYVSATKVKSVDKFLAHDLIYNINDKKLKNYDKVKTELLNEDLAKKYKDE | 80 |
| SEC-4446 (SEQ. ID. NO:6) | 1 | ESQPDPMPDDLHKSSEFTGTMGNMKYLYDDHYVSATKVKSVDKFLAHDLIYNISDKRLKNYDKVKTELLNEDLAKKYKDE | 80 |
| SEC-bovine (SEQ. ID. NO:7) | 1 | ESQPDPTPDELHKASKFTGLMENMKVLYDDRYVSATKVKSVDKFLAHDLIYNISDKKLKNYDKVKTELLNEDLAKKYKDE | 80 |
| SEC-ovine (SEQ. ID. NO:8) | 1 | ESQPDPTPDELHKASKFTGLMENMKVLYDDRYVSATKVKSVDKFLAHDLIYNISDKKLKNYDKVKTELLNEDLAKKYKDE | 80 |
| | | 120 | |
| | | * * ? * * | |
| SEC1 | 81 | VVDVYGSNYYVNCYFSSKDNVGKVTGGKTCMYGGITKHEGNHFDNGNLQNVLIRVYENKRNTISFEVQTDKKSVTAQELD | 160 |
| SEC2 | 81 | VVDVYGSNYYVNCYFSSKDNVGKVTGGKTCMYGGITKHEGNHFDNGNLQNVLIRVYENKRNTISFEVQTDKKSVTAQELD | 160 |
| SEC3-FR1913 | 81 | VVDVYGSNYYVNCYFSSKDNVGKVTGGKTCMYGGITKHEGNHFDNGNLQNVLYRVYENKRNTISFEVQTDKKSVTAQELD | 160 |
| SEC3-FR1909 | 81 | VVDVYGSNYYVNCYFSSKDNVGKVTGGKTCMYGGITKHEGNHFDNGNLQNVLIRVYENKRNTISFEVQTDKKSVTAQELD | 160 |
| SEC-MNCopeland | 81 | VVDVYGSNYYVNCYFSSKDNVGKVTGGKTCMYGGITKHEGNHFDNGNLQNVLIRVYENKRNTISFEVQTDKKSVTAQELD | 160 |
| SEC-4446 | 81 | VVDVYGSNYYVNCYFSSKDNVGKVTGGKTCMYGGITKHEGNHFDNGNLQNVLVRVYENKRNTISFEVQTDKKSVTAQELD | 160 |
| SEC-bovine | 81 | VVDVYGSNYYVNCYFFSKDNVGKVTGGKTCMYGGITKHEGNHFDNGNLQNVLIRVYENKRNTISFEVQTDKKSVTAQELD | 160 |
| SEC-ovine | 81 | VVDVYGSNYYVNCCFFSKDNVGKVTGGKTCMYGGITKHEGNHFDNGNLQNVLIRVYENKRNTISFEVQTDKKSVTAQELD | 160 |
| | | 200 | |
| | | * * ? * * * * | |
| SEC1 | 161 | IKARNFLINKKNLYEFNSSPYETGYIKFIENNGNTFWYDMMPAPGDKFDQSKYLMMYNDNKTVDSKSVKIEVHLTTKNGX | 240 |
| SEC2 | 161 | IKARNFLINKKNLYEFNSSPYETGYIKFIENNGNTFQYDMMPAPGDKFDQSKVLMMYNDNKTVDSKSVKIEVHLTTKNGX | 240 |
| SEC3-FR1913 | 161 | IKARNFLINKKNLYEFNSSPYETGYIKFIENNGNTFQYDMMPAPGDKFDQSKYLMMYNDNKTVDSKSVKIEVHLTTKNGX | 240 |
| SEC3-FR1909 | 161 | IKARNFLINKKNLYEFNSSPYETGYIKFIESNGNTFWYDMMPAPGDKFDQSKYLMIYKDNKMVDSKSVKIEVHLTTKNGX | 240 |
| SEC-MNCopeland | 161 | IKARNFLINKKNLYEFNSSPYETGYIKFIENNGNTFQYDMMPAPGDKFDQSKYLMMYNDNKTVDSKRVKIEVHLTTKNGX | 240 |
| SEC-4446 | 161 | IKARNFLINKKNLYEFNSSPYETGYIKFIENNGNTFQYDMMPAPGDKFDQSKYLMMYNDNKTVDSKRVKIEVHLTTKNGX | 240 |
| SEC-bovine | 161 | IKARNFLINKKNLYEFNSSPYETGYIKFIENNGNTFQYDMMPAPGDKFDQSKYLMMYNDNKTVDSKRVKIEVHLTTKNGX | 240 |
| SEC-ovine | 161 | IKARNFLINKKNLYEFNSSPYETGYIKFIENNGNTFQYDMMPAPGDKFDQSKYLMMYNDNKTVDSKRVKIEVHLTTKNGX | 240 |

TABLE 3A

Conserved Regions of Enterotoxin Molecules*

| Toxin | Residue # | | |
|---|---|---|---|
| | | Region 1 | |
| SEA | 79 | K Y K G K K V D L Y G | (SEQ. ID. NO:18) |
| SEB | 76 | K Y K D K Y V D V F G | (SEQ. ID. NO:19) |
| SEC1 | 76 | K Y K D E V V D V Y G | (SEQ. ID. NO:20) |
| SEC2 | 76 | K Y K D E V V D V Y G | (SEQ. ID. NO:21) |
| SEC3 | 76 | K Y K D E V V D V Y G | (SEQ. ID. NO:22) |
| SED | 74 | H F K S K N V D V Y P | (SEQ. ID. NO:23) |
| SEE | 76 | K Y K G K K V D L Y G | (SEQ. ID. NO:24) |
| SPEA | 70 | L F K D K N V D I Y G | (SEQ. ID. NO:25) |
| SPEC | 63 | F K R D D H V D V F G | (SEQ. ID. NO:26) |
| TSST-1 | 56 | F T K G E K V D L N T | (SEQ. ID. NO:27) |
| | | Region 3 | |
| SEA | 147 | K K N V T V Q E L D L Q A R R Y L | (SEQ. ID. NO:28) |
| SEB | 152 | K K K V T A Q E L D Y L T R H Y L | (SEQ. ID. NO:29) |
| SEC1 | 151 | K K S V T A Q E L D I K A R N F L | (SEQ. ID. NO:30) |
| SEC2 | 151 | K K S V T A Q E L D I K A R N F L | (SEQ. ID. NO:31) |
| SEC3 | 151 | K K S V T A Q E L D I K A R N F L | (SEQ. ID. NO:32) |
| SED | 142 | K K N V T V Q E L D A Q A R R Y L | (SEQ. ID. NO:33) |
| SEE | 144 | K K E V T V Q E L D L Q A R H Y L | (SEQ. ID. NO:34) |
| SPEA | 137 | K K M V T A Q E L D Y K V R K Y L | (SEQ. ID. NO:35) |
| SPEC | 124 | K D I V T F Q E I D F K I R K Y L | (SEQ. ID. NO:36) |
| TSST-1 | 121 | K K - - - - Q - L - I | (SEQ. ID. NO:37) |
| TSST-1 | 129 | L D F E I R H Q L | (SEQ. ID. NO:38) |

*From Hoffmann et al., Infect Immunol 62:3396 (1994).

TABLE 3B

Conserved Regions of Enterotoxin Molecules (Cont.)*

| Toxin | Residue # | | |
|---|---|---|---|
| | | Region 2 | |
| SEA | 106 | C M Y G G V I L H D N N | (SEQ. ID. NO:39) |
| SEB | 113 | C M Y G G V T E H N G N | (SEQ. ID. NO:40) |
| SEC1 | 110 | C M Y G G I T K H E G N | (SEQ. ID. NO:41) |
| SEC2 | 110 | C M Y G G I T K H E G N | (SEQ. ID. NO:42) |
| SEC3 | 110 | C M Y G G I T K H E G N | (SEQ. ID. NO:43) |
| SED | 101 | C T Y G G V T P H E G N | (SEQ. ID. NO:44) |
| SEE | 103 | C M Y G G V T L H D N N | (SEQ. ID. NO:45) |
| SPEA | 98 | C I Y G G V T N H E G N | (SEQ. ID. NO:46) |
| SPEC | 85 | Y I Y G G I T P A Q N N | (SEQ. ID. NO:47) |
| TSST-1 | 83 | F Q I S G V T N T E K L | (SEQ. ID. NO:48) |
| | | Region 4 | |
| SEA | 209 | L L R I Y R D N K T I N S E | (SEQ. ID. NO:49) |
| SEB | 213 | Y L M M V N D N K M V D S K | (SEQ. ID. NO:50) |
| SEC1 | 213 | Y L M M Y N D N K T V D S K | (SEQ. ID. NO:51) |
| SEC2 | 213 | Y L M M Y N D N K T V D S K | (SEQ. ID. NO:52) |
| SEC3 | 213 | Y L M I Y K D N K M V D S K | (SEQ. ID. NO:53) |
| SED | 204 | Q L R I Y S D N K T L S T E | (SEQ. ID. NO:54) |
| SEE | 206 | L L R I Y R D N K T I N S E | (SEQ. ID. NO:55) |
| SPEA | 197 | Y L M I Y K D M E T L D S N | (SEQ. ID. NO:56) |
| SPEC | 184 | I F A K Y K D N R I I N M K | (SEQ. ID. NO:57) |
| TSST-1 | 179 | P P I N I D E I K T I E A E | (SEQ. ID. NO:58) |

*From Hoffmann et al., Infect Immunol 62:3396 (1994).

TABLE 4

SEC1 LOOP MUTANTS

| AMINO ACID # | 93 | 94 | 95 | 96 | 97 | 98 | 99 | 100 | 101 | 102 | 103 | 104 | 105 | 106 | 107 | 108 | 109 | 110 | |
|---|---|---|---|---|---|---|---|---|---|---|---|---|---|---|---|---|---|---|---|
| SEC1 (wild type) | | | | | | | | | | | | | | | | | | | |
| AMINO ACID | Cys | Tyr | Phe | Ser | Ser | Lys | Asp | Asn | Val | Gly | Lys | Val | Thr | Gly | Gly | Lys | Thr | Cys | (SEQ. ID. NO:60) |
| NUCLEIC ACID | TGC | TAT | TTT | TCA | TCC | AAA | GAT | AAT | GTA | GGT | AAA | GTT | ACA | GGT | GGC | AAA | ACT | TGT | (SEQ. ID. NO:59) |
| SEC1 Loop Deletion Mutants | | | | | | | | | 301 | - | 306 | | | | | | | | |

TABLE 4-continued

SEC1 LOOP MUTANTS

| 4 A.A. MUTANT | Cys Tyr Phe Ser Ser Lys Asp Asn Ala | Gly Gly Lys Thr Cys | (SEQ. ID. NO:62) |
|---|---|---|---|
| | TGC TAT TTT TCA TCC AAA GAT AAT GCA ------- | GGT GGC AAA ACT TGT | (SEQ. ID. NO:61) |
| 9 A.A. MUTANT | Cys Tyr Phe Ser Ser | Gly Lys Thr Cys | (SEQ. ID. NO:64) |
| | TGC TAT TTT TCA TCC --------------- | GGC AAA ACT TGT | (SEQ. ID. NO:63) |
| 12 A.A MUTANT | Cys Cys | Gly Lys Thr Cys | (SEQ. ID. NO:66) |
| | TGC T-- -------------------- | GT GGC AAA ACT TGT | (SEQ. ID. NO:65) |

What is claimed is:

1. A toxin, comprising a polypeptide sequence selected from the group, consisting of SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8; wherein the polypeptide sequence is mutated in the region from residue 93 to residue 110 to contain no more than 10 amino acid residues; wherein toxicity is reduced in comparison to the unmutated native toxin.

2. The toxin of claim 1 wherein the polypeptide sequence is mutated in the region from residue 93 to residue 110 to contain no more than 6 amino acid residues.

3. The toxin of claim 1, wherein the polypeptide sequence comprises SEQ ID NO: 1 and the mutation comprises deletion of amino acid residues 95–106 of SEQ ID NO: 1.

4. The toxin of claim 1, wherein the polypeptide sequence comprises SEQ ID NO: 1 and the mutation further comprises a cysteine residue at position 94 of SEQ ID NO: 1.

5. The toxin of claim 1 having an emetic response inducing activity decreased by at least 100-fold in comparison to the native toxin.

6. The toxin of claim 1 having a fever inducing activity decreased by at least 100-fold in comparison to the native toxin.

7. The toxin of claim 1 having an LD50 in Dutch Belted rabbits which is at least 100-fold higher than the native toxin.

8. A *staphylococcal* toxin, comprising an amino acid sequence of a Type C *staphylococcal* toxin having a disulfide loop region wherein at least 40% of the amino acid residues within the disulfide loop region are deleted and wherein toxicity is reduced in comparison to the unmutated native toxin.

9. The *staphylococcal* toxin of claim 8 comprising a cysteine residue at position 2 of the disulfide loop region, wherein the disulfide loop region, before deletion of at least 40% of the amino acid residues, is selected from the group consisting of SEQ ID NO: 9, SEQ ID NO: 10, SEQ ID NO: 11, SEQ ID NO: 12, SEQ ID NO: 13, SEQ ID NO:14, SEQ ID NO: 15, SEQ ID NO: 16, and SEQ ID NO: 17.

10. A *staphylococcal* toxin, wherein the *staphylococcal* toxin comprises a disulfide loop region comprising SEQ ID NO: 66 (Cys-Cys-Gly-Lys-Thr-Cys)and wherein toxicity is reduced in comparison to the unmutated native toxin.

11. The toxin of claim 1, wherein the polypeptide sequence comprises SEQ ID NO: 1 and the mutation comprises a deletion of amino acid residues 98–106 of SEQ ID NO: 1.

12. The toxin of claim 11 wherein the mutation comprises deletion of at least 12 amino acid residues in the region from residue 93 to residue 110.

* * * * *

SEQUENCE LISTING

<160> NUMBER OF SEQ ID NOS: 66

<210> SEQ ID NO 1
<211> LENGTH: 240
<212> TYPE: PRT
<213> ORGANISM: Staphylococcus aureus
<220> FEATURE:
<221> NAME/KEY: MISC_FEATURE
<222> LOCATION: (240)..(240)
<223> OTHER INFORMATION: Xaa is unknown.

<400> SEQUENCE: 1

```
Glu Ser Gln Pro Asp Pro Thr Pro Asp Glu Leu His Lys Ala Ser Lys
1               5                   10                  15

Phe Thr Gly Leu Met Glu Asn Met Lys Val Leu Tyr Asp Asp His Tyr
            20                  25                  30

Val Ser Ala Thr Lys Val Lys Ser Val Asp Lys Phe Leu Ala His Asp
        35                  40                  45

Leu Ile Tyr Asn Ile Ser Asp Lys Lys Leu Lys Asn Tyr Asp Lys Val
    50                  55                  60

Lys Thr Glu Leu Leu Asn Glu Gly Leu Ala Lys Lys Tyr Lys Asp Glu
65                  70                  75                  80

Val Val Asp Val Tyr Gly Ser Asn Tyr Tyr Val Asn Cys Tyr Phe Ser
                85                  90                  95

Ser Lys Asp Asn Val Gly Lys Val Thr Gly Gly Lys Thr Cys Met Tyr
            100                 105                 110

Gly Gly Ile Thr Lys His Glu Gly Asn His Phe Asp Asn Gly Asn Leu
        115                 120                 125

Gln Asn Val Leu Ile Arg Val Tyr Glu Asn Lys Arg Asn Thr Ile Ser
130                 135                 140

Phe Glu Val Gln Thr Asp Lys Lys Ser Val Thr Ala Gln Glu Leu Asp
145                 150                 155                 160

Ile Lys Ala Arg Asn Phe Leu Ile Asn Lys Lys Asn Leu Tyr Glu Phe
                165                 170                 175

Asn Ser Ser Pro Tyr Glu Thr Gly Tyr Ile Lys Phe Ile Glu Asn Asn
            180                 185                 190

Gly Asn Thr Phe Trp Tyr Asp Met Met Pro Ala Pro Gly Asp Lys Phe
        195                 200                 205

Asp Gln Ser Lys Tyr Leu Met Met Tyr Asn Asp Asn Lys Thr Val Asp
    210                 215                 220

Ser Lys Ser Val Lys Ile Glu Val His Leu Thr Thr Lys Asn Gly Xaa
225                 230                 235                 240
```

<210> SEQ ID NO 2
<211> LENGTH: 240
<212> TYPE: PRT

<213> ORGANISM: Staphylococcus aureus
<220> FEATURE:
<221> NAME/KEY: MISC_FEATURE
<222> LOCATION: (240)..(240)
<223> OTHER INFORMATION: Xaa is unknown.

<400> SEQUENCE: 2

```
Glu Ser Gln Pro Asp Pro Thr Pro Asp Glu Leu His Lys Ser Ser Glu
1               5                   10                  15

Phe Thr Gly Thr Met Gly Asn Met Lys Tyr Leu Tyr Asp Asp His Tyr
            20                  25                  30

Val Ser Ala Thr Lys Val Met Ser Val Asp Lys Phe Leu Ala His Asp
        35                  40                  45

Leu Ile Tyr Asn Ile Ser Asp Lys Lys Leu Lys Asn Tyr Asp Lys Val
    50                  55                  60

Lys Thr Glu Leu Leu Asn Glu Asp Leu Ala Lys Lys Tyr Lys Asp Glu
65                  70                  75                  80

Val Val Asp Val Tyr Gly Ser Asn Tyr Tyr Val Asn Cys Tyr Phe Ser
                85                  90                  95

Ser Lys Asp Asn Val Gly Lys Val Thr Gly Gly Lys Thr Cys Met Tyr
            100                 105                 110

Gly Gly Ile Thr Lys His Glu Gly Asn His Phe Asp Asn Gly Asn Leu
        115                 120                 125

Gln Asn Val Leu Ile Arg Val Tyr Glu Asn Lys Arg Asn Thr Ile Ser
    130                 135                 140

Phe Glu Val Gln Thr Asp Lys Lys Ser Val Thr Ala Gln Glu Leu As
145                 150                 155                 160

Ile Lys Ala Arg Asn Phe Leu Ile Asn Lys Lys Asn Leu Tyr Glu Phe
                165                 170                 175

Asn Ser Ser Pro Tyr Glu Thr Gly Tyr Ile Lys Phe Ile Glu Asn Asn
            180                 185                 190

Gly Asn Thr Phe Gln Tyr Asp Met Met Pro Ala Pro Gly Asp Lys Phe
        195                 200                 205

Asp Gln Ser Lys Tyr Leu Met Met Tyr Asn Asp Asn Lys Thr Val Asp
    210                 215                 220

Ser Lys Ser Val Lys Ile Glu Val His Leu Thr Thr Lys Asn Gly Xaa
225                 230                 235                 240
```

<210> SEQ ID NO 3
<211> LENGTH: 240
<212> TYPE: PRT
<213> ORGANISM: Staphylococcus aureus
<220> FEATURE:
<221> NAME/KEY: MISC_FEATURE
<222> LOCATION: (240)..(240)
<223> OTHER INFORMATION: Xaa is unknown.

<400> SEQUENCE: 3

```
Glu Ser Gln Pro Asp Pro Met Pro Asp Asp Leu His Lys Ser Ser Glu
1               5                   10                  15

Phe Thr Gly Thr Met Gly Asn Met Lys Tyr Leu Tyr Asp Asp His Tyr
            20                  25                  30

Val Ser Ala Thr Lys Val Lys Ser Val Asp Lys Phe Leu Ala His Asp
        35                  40                  45

Leu Ile Tyr Asn Ile Ser Asp Lys Lys Leu Lys Asn Tyr Asp Lys Val
    50                  55                  60

Lys Thr Glu Leu Leu Asn Glu Asp Leu Ala Lys Lys Tyr Lys Asp Glu
65                  70                  75                  80
```

-continued

```
Val Val Asp Val Tyr Gly Ser Asn Tyr Tyr Val Asn Cys Tyr Phe Ser
            85                  90                  95

Ser Lys Asp Asn Val Gly Lys Val Thr Gly Lys Thr Cys Met Tyr
        100                 105                 110

Gly Gly Ile Thr Lys His Glu Gly Asn His Phe Asp Asn Gly Asn Leu
            115                 120                 125

Gln Asn Val Leu Val Arg Val Tyr Glu Asn Lys Arg Asn Thr Ile Ser
    130                 135                 140

Phe Glu Val Gln Thr Asp Lys Lys Ser Val Thr Ala Gln Glu Leu As
145                 150                 155                 160

Ile Lys Ala Arg Asn Phe Leu Ile Asn Lys Lys Asn Leu Tyr Glu Phe
                165                 170                 175

Asn Ser Ser Pro Tyr Glu Thr Gly Tyr Ile Lys Phe Ile Glu Asn Asn
            180                 185                 190

Gly Asn Thr Phe Gln Tyr Asp Met Met Pro Ala Pro Gly Asp Lys Phe
        195                 200                 205

Asp Gln Ser Lys Tyr Leu Met Met Tyr Asn Asp Asn Lys Thr Val Asp
    210                 215                 220

Ser Lys Ser Val Lys Ile Glu Val His Leu Thr Thr Lys Asn Gly Xaa
225                 230                 235                 240
```

<210> SEQ ID NO 4
<211> LENGTH: 240
<212> TYPE: PRT
<213> ORGANISM: Staphylococcus aureus
<220> FEATURE:
<221> NAME/KEY: MISC_FEATURE
<222> LOCATION: (240)..(240)
<223> OTHER INFORMATION: Xaa is unknown.

<400> SEQUENCE: 4

```
Glu Ser Gln Pro Asp Pro Met Pro Asp Asp Leu His Lys Ser Ser Glu
1               5                   10                  15

Phe Thr Gly Thr Met Gly Asn Met Lys Tyr Leu Tyr Asp Asp His Tyr
            20                  25                  30

Val Ser Ala Thr Lys Val Lys Ser Val Asp Lys Phe Leu Ala His Asp
        35                  40                  45

Leu Ile Tyr Asn Ile Asn Asp Lys Lys Leu Asn Asn Tyr Asp Lys Val
    50                  55                  60

Lys Thr Glu Leu Leu Asn Glu Asp Leu Ala Asn Lys Tyr Lys Asp Glu
65                  70                  75                  80

Val Val Asp Val Tyr Gly Ser Asn Tyr Tyr Val Asn Cys Tyr Phe Ser
            85                  90                  95

Ser Lys Asp Asn Val Gly Lys Val Thr Ser Gly Lys Thr Cys Met Tyr
        100                 105                 110

Gly Gly Ile Thr Lys His Glu Gly Asn His Phe Asp Asn Gly Asn Leu
            115                 120                 125

Gln Asn Val Leu Ile Arg Val Tyr Glu Asn Lys Arg Asn Thr Ile Ser
    130                 135                 140

Phe Glu Val Gln Thr Asp Lys Lys Ser Val Thr Ala Gln Glu Leu As
145                 150                 155                 160

Ile Lys Ala Arg Asn Phe Leu Ile Asn Lys Lys Asn Leu Tyr Glu Phe
                165                 170                 175

Asn Ser Ser Pro Tyr Glu Thr Gly Tyr Ile Lys Phe Ile Glu Ser Asn
            180                 185                 190
```

```
Gly Asn Thr Phe Trp Tyr Asp Met Met Pro Ala Pro Gly Asp Lys Phe
        195                 200                 205

Asp Gln Ser Lys Tyr Leu Met Ile Tyr Lys Asp Asn Lys Met Val Asp
        210                 215                 220

Ser Lys Ser Val Lys Ile Glu Val His Leu Thr Thr Lys Asn Gly Xaa
225                 230                 235                 240

<210> SEQ ID NO 5
<211> LENGTH: 240
<212> TYPE: PRT
<213> ORGANISM: Staphylococcus aureus
<220> FEATURE:
<221> NAME/KEY: MISC_FEATURE
<222> LOCATION: (240)..(240)
<223> OTHER INFORMATION: Xaa is unknown.

<400> SEQUENCE: 5

Glu Ser Gln Pro Asp Pro Thr Pro Asp Glu Leu His Lys Ser Ser Glu
1               5                   10                  15

Phe Thr Gly Thr Met Gly Asn Met Lys Tyr Leu Tyr Asp Asp His Tyr
            20                  25                  30

Val Ser Ala Thr Lys Val Lys Ser Val Asp Lys Phe Leu Ala His Asp
        35                  40                  45

Leu Ile Tyr Asn Ile Ser Asp Lys Lys Leu Lys Asn Tyr Asp Lys Val
50                  55                  60

Lys Thr Glu Leu Leu Asn Glu Asp Leu Ala Lys Lys Tyr Lys Asp Glu
65                  70                  75                  80

Val Val Asp Val Tyr Gly Ser Asn Tyr Tyr Val Asn Cys Tyr Phe Ser
                85                  90                  95

Ser Lys Asp Asn Val Gly Lys Val Thr Gly Gly Lys Thr Cys Met Tyr
            100                 105                 110

Gly Gly Ile Thr Lys His Glu Gly Asn His Phe Asp Asn Gly Asn Leu
        115                 120                 125

Gln Asn Val Leu Ile Arg Val Tyr Glu Asn Lys Arg Asn Thr Ile Ser
    130                 135                 140

Phe Glu Val Gln Thr Asp Lys Lys Ser Val Thr Ala Gln Glu Leu As
145                 150                 155                 160

Ile Lys Ala Arg Asn Phe Leu Ile Asn Lys Lys Asn Leu Tyr Glu Phe
                165                 170                 175

Asn Ser Ser Pro Tyr Glu Thr Gly Tyr Ile Lys Phe Ile Glu Asn Asn
            180                 185                 190

Gly Asn Thr Phe Gln Tyr Asp Met Met Pro Ala Pro Gly Asp Lys Phe
        195                 200                 205

Asp Gln Ser Lys Tyr Leu Met Met Tyr Asn Asp Asn Lys Thr Val Asp
        210                 215                 220

Ser Lys Arg Val Lys Ile Glu Val His Leu Thr Thr Lys Asn Gly Xaa
225                 230                 235                 240

<210> SEQ ID NO 6
<211> LENGTH: 240
<212> TYPE: PRT
<213> ORGANISM: Staphylococcus aureus
<220> FEATURE:
<221> NAME/KEY: MISC_FEATURE
<222> LOCATION: (240)..(240)
<223> OTHER INFORMATION: Xaa is unknown.

<400> SEQUENCE: 6

Glu Ser Gln Pro Asp Pro Met Pro Asp Asp Leu His Lys Ser Ser Glu
```

-continued

```
                1               5                  10                 15
Phe Thr Gly Thr Met Gly Asn Met Lys Tyr Leu Tyr Asp Asp His Tyr
                20                  25                 30

Val Ser Ala Thr Lys Val Lys Ser Val Asp Lys Phe Leu Ala His Asp
                35                  40                 45

Leu Ile Tyr Asn Ile Ser Asp Lys Arg Leu Lys Asn Tyr Asp Lys Val
            50                  55                  60

Lys Thr Glu Leu Leu Asn Glu Asp Leu Ala Lys Lys Tyr Lys Asp Glu
65                      70                  75                  80

Val Val Asp Val Tyr Gly Ser Asn Tyr Tyr Val Asn Cys Tyr Phe Ser
                    85                  90                  95

Ser Lys Asp Asn Val Gly Lys Val Thr Gly Gly Lys Thr Cys Met Tyr
                100                 105                 110

Gly Gly Ile Thr Lys His Glu Gly Asn His Phe Asp Asn Gly Asn Leu
                115                 120                 125

Gln Asn Val Leu Val Arg Val Tyr Glu Asn Lys Arg Asn Thr Ile Ser
                130                 135                 140

Phe Glu Val Gln Thr Asp Lys Lys Ser Val Thr Ala Gln Glu Leu As
145                 150                 155                 160

Ile Lys Ala Arg Asn Phe Leu Ile Asn Lys Lys Asn Leu Tyr Glu Phe
                    165                 170                 175

Asn Ser Ser Pro Tyr Glu Thr Gly Tyr Ile Lys Phe Ile Glu Asn Asn
                    180                 185                 190

Gly Asn Thr Phe Gln Tyr Asp Met Met Pro Ala Pro Gly Asp Lys Phe
                    195                 200                 205

Asp Gln Ser Lys Tyr Leu Met Met Tyr Asn Asp Asn Lys Thr Val Asp
                210                 215                 220

Ser Lys Arg Val Lys Ile Glu Val His Leu Thr Thr Lys Asn Gly Xaa
225                 230                 235                 240
```

<210> SEQ ID NO 7
<211> LENGTH: 240
<212> TYPE: PRT
<213> ORGANISM: Staphylococcus aureus
<220> FEATURE:
<221> NAME/KEY: MISC_FEATURE
<222> LOCATION: (240)..(240)
<223> OTHER INFORMATION: Xaa is unknown.

<400> SEQUENCE: 7

```
Glu Ser Gln Pro Asp Pro Thr Pro Asp Glu Leu His Lys Ala Ser Lys
1               5                   10                  15

Phe Thr Gly Leu Met Glu Asn Met Lys Val Leu Tyr Asp Asp Arg Tyr
                20                  25                  30

Val Ser Ala Thr Lys Val Lys Ser Val Asp Lys Phe Leu Ala His Asp
                35                  40                  45

Leu Ile Tyr Asn Ile Ser Asp Lys Lys Leu Lys Asn Tyr Asp Lys Val
            50                  55                  60

Lys Thr Glu Leu Leu Asn Glu Asp Leu Ala Lys Lys Tyr Lys Asp Glu
65                      70                  75                  80

Val Val Asp Val Tyr Gly Ser Asn Tyr Tyr Val Asn Cys Tyr Phe Phe
                    85                  90                  95

Ser Lys Asp Asn Val Gly Lys Val Thr Gly Gly Lys Thr Cys Met Tyr
                100                 105                 110

Gly Gly Ile Thr Lys His Glu Gly Asn His Phe Asp Asn Gly Asn Leu
                115                 120                 125
```

Gln Asn Val Leu Ile Arg Val Tyr Glu Asn Lys Arg Asn Thr Ile Ser
    130                 135                 140

Phe Glu Val Gln Thr Asp Lys Lys Ser Val Thr Ala Gln Glu Leu As
145                 150                 155                 160

Ile Lys Ala Arg Asn Phe Leu Ile Asn Lys Lys Asn Leu Tyr Glu Phe
                165                 170                 175

Asn Ser Ser Pro Tyr Glu Thr Gly Tyr Ile Lys Phe Ile Glu Asn Asn
            180                 185                 190

Gly Asn Thr Phe Gln Tyr Asp Met Met Pro Ala Pro Gly Asp Lys Phe
        195                 200                 205

Asp Gln Ser Lys Tyr Leu Met Met Tyr Asn Asp Asn Lys Thr Val Asp
    210                 215                 220

Ser Lys Arg Val Lys Ile Glu Val His Leu Thr Thr Lys Asn Gly Xaa
225                 230                 235                 240

<210> SEQ ID NO 8
<211> LENGTH: 240
<212> TYPE: PRT
<213> ORGANISM: Staphylococcus aureus
<220> FEATURE:
<221> NAME/KEY: MISC_FEATURE
<222> LOCATION: (240)..(240)
<223> OTHER INFORMATION: Xaa is unknown.

<400> SEQUENCE: 8

Glu Ser Gln Pro Asp Pro Thr Pro Asp Glu Leu His Lys Ala Ser Lys
1               5                   10                  15

Phe Thr Gly Leu Met Glu Asn Met Lys Val Leu Tyr Asp Asp Arg Tyr
            20                  25                  30

Val Ser Ala Thr Lys Val Lys Ser Val Asp Lys Phe Leu Ala His Asp
        35                  40                  45

Leu Ile Tyr Asn Ile Ser Asp Lys Lys Leu Lys Asn Tyr Asp Lys Val
    50                  55                  60

Lys Thr Glu Leu Leu Asn Glu Asp Leu Ala Lys Lys Tyr Lys Asp Glu
65                  70                  75                  80

Val Val Asp Val Tyr Gly Ser Asn Tyr Tyr Val Asn Cys Cys Phe Phe
                85                  90                  95

Ser Lys Asp Asn Val Gly Lys Val Thr Gly Gly Lys Thr Cys Met Tyr
            100                 105                 110

Gly Gly Ile Thr Lys His Glu Gly Asn His Phe Asp Asn Gly Asn Leu
        115                 120                 125

Gln Asn Val Leu Ile Arg Val Tyr Glu Asn Lys Arg Asn Thr Ile Ser
    130                 135                 140

Phe Glu Val Gln Thr Asp Lys Lys Ser Val Thr Ala Gln Glu Leu As
145                 150                 155                 160

Ile Lys Ala Arg Asn Phe Leu Ile Asn Lys Lys Asn Leu Tyr Glu Phe
                165                 170                 175

Asn Ser Ser Pro Tyr Glu Thr Gly Tyr Ile Lys Phe Ile Glu Asn Asn
            180                 185                 190

Gly Asn Thr Phe Gln Tyr Asp Met Met Pro Ala Pro Gly Asp Lys Phe
        195                 200                 205

Asp Gln Ser Lys Tyr Leu Met Met Tyr Asn Asp Asn Lys Thr Val Asp
    210                 215                 220

Ser Lys Arg Val Lys Ile Glu Val His Leu Thr Thr Lys Asn Gly Xaa
225                 230                 235                 240

```
<210> SEQ ID NO 9
<211> LENGTH: 11
<212> TYPE: PRT
<213> ORGANISM: Staphylococcus aureus

<400> SEQUENCE: 9

Cys Ala Gly Gly Thr Pro Asn Lys Thr Ala Cys
1               5                   10

<210> SEQ ID NO 10
<211> LENGTH: 21
<212> TYPE: PRT
<213> ORGANISM: Staphylococcus aureus

<400> SEQUENCE: 10

Cys Tyr Phe Ser Lys Lys Thr Asn Asp Ile Asn Ser His Gln Thr Pro
1               5                   10                  15

Lys Arg Lys Thr Cys
            20

<210> SEQ ID NO 11
<211> LENGTH: 18
<212> TYPE: PRT
<213> ORGANISM: Staphylococcus aureus

<400> SEQUENCE: 11

Cys Tyr Phe Ser Ser Lys Asp Asn Val Gly Lys Val Thr Gly Gly Lys
1               5                   10                  15

Thr Cys

<210> SEQ ID NO 12
<211> LENGTH: 18
<212> TYPE: PRT
<213> ORGANISM: Staphylococcus aureus

<400> SEQUENCE: 12

Cys Tyr Phe Ser Ser Lys Asp Asn Val Gly Lys Val Thr Gly Gly Lys
1               5                   10                  15

Thr Cys

<210> SEQ ID NO 13
<211> LENGTH: 18
<212> TYPE: PRT
<213> ORGANISM: Staphylococcus aureus

<400> SEQUENCE: 13

Cys Tyr Phe Ser Ser Lys Asp Asn Val Gly Lys Val Thr Gly Gly Lys
1               5                   10                  15

Thr Cys

<210> SEQ ID NO 14
<211> LENGTH: 18
<212> TYPE: PRT
<213> ORGANISM: Staphylococcus aureus

<400> SEQUENCE: 14

Cys Tyr Phe Ser Ser Lys Asp Asn Val Gly Lys Val Thr Ser Gly Lys
1               5                   10                  15

Thr Cys

<210> SEQ ID NO 15
```

```
<211> LENGTH: 18
<212> TYPE: PRT
<213> ORGANISM: Staphylococcus aureus

<400> SEQUENCE: 15

Cys Tyr Phe Ser Ser Lys Asp Asn Val Gly Lys Val Thr Gly Gly Lys
1               5                   10                  15

Thr Cys

<210> SEQ ID NO 16
<211> LENGTH: 18
<212> TYPE: PRT
<213> ORGANISM: Staphylococcus aureus

<400> SEQUENCE: 16

Cys Tyr Phe Ser Ser Lys Asp Asn Val Gly Lys Val Thr Gly Gly Lys
1               5                   10                  15

Thr Cys

<210> SEQ ID NO 17
<211> LENGTH: 18
<212> TYPE: PRT
<213> ORGANISM: Staphylococcus aureus

<400> SEQUENCE: 17

Cys Cys Phe Ser Ser Lys Asp Asn Val Gly Lys Val Thr Gly Gly Lys
1               5                   10                  15

Thr Cys

<210> SEQ ID NO 18
<211> LENGTH: 11
<212> TYPE: PRT
<213> ORGANISM: Staphylococcus aureus

<400> SEQUENCE: 18

Lys Tyr Lys Gly Lys Lys Val Asp Leu Tyr Gly
1               5                   10

<210> SEQ ID NO 19
<211> LENGTH: 11
<212> TYPE: PRT
<213> ORGANISM: Staphylococcus aureus

<400> SEQUENCE: 19

Lys Tyr Lys Asp Lys Tyr Val Asp Val Phe Gly
1               5                   10

<210> SEQ ID NO 20
<211> LENGTH: 11
<212> TYPE: PRT
<213> ORGANISM: Staphylococcus aureus

<400> SEQUENCE: 20

Lys Tyr Lys Asp Glu Val Val Asp Val Tyr Gly
1               5                   10

<210> SEQ ID NO 21
<211> LENGTH: 11
<212> TYPE: PRT
<213> ORGANISM: Staphylococcus aureus

<400> SEQUENCE: 21

Lys Tyr Lys Asp Glu Val Val Asp Val Tyr Gly
```

```
<210> SEQ ID NO 22
<211> LENGTH: 11
<212> TYPE: PRT
<213> ORGANISM: Staphylococcus aureus

<400> SEQUENCE: 22

Lys Tyr Lys Asp Glu Val Val Asp Val Tyr Gly
1               5                   10

<210> SEQ ID NO 23
<211> LENGTH: 11
<212> TYPE: PRT
<213> ORGANISM: Staphylococcus aureus

<400> SEQUENCE: 23

His Phe Lys Ser Lys Asn Val Asp Val Tyr Pro
1               5                   10

<210> SEQ ID NO 24
<211> LENGTH: 11
<212> TYPE: PRT
<213> ORGANISM: Staphylococcus aureus

<400> SEQUENCE: 24

Lys Tyr Lys Gly Lys Lys Val Asp Leu Tyr Gly
1               5                   10

<210> SEQ ID NO 25
<211> LENGTH: 11
<212> TYPE: PRT
<213> ORGANISM: Streptococcus pyrogenes

<400> SEQUENCE: 25

Leu Phe Lys Asp Lys Asn Val Asp Ile Tyr Gly
1               5                   10

<210> SEQ ID NO 26
<211> LENGTH: 11
<212> TYPE: PRT
<213> ORGANISM: Streptococcus pyrogenes

<400> SEQUENCE: 26

Phe Lys Arg Asp Asp His Val Asp Val Phe Gly
1               5                   10

<210> SEQ ID NO 27
<211> LENGTH: 11
<212> TYPE: PRT
<213> ORGANISM: Staphylococcus aureus

<400> SEQUENCE: 27

Phe Thr Lys Gly Glu Lys Val Asp Leu Asn Thr
1               5                   10

<210> SEQ ID NO 28
<211> LENGTH: 17
<212> TYPE: PRT
<213> ORGANISM: Staphylococcus aureus

<400> SEQUENCE: 28

Lys Lys Asn Val Thr Val Gln Glu Leu Asp Leu Gln Ala Arg Arg Tyr
1               5                   10                  15
```

Leu

```
<210> SEQ ID NO 29
<211> LENGTH: 17
<212> TYPE: PRT
<213> ORGANISM: Staphylococcus aureus

<400> SEQUENCE: 29
```

Lys Lys Lys Val Thr Ala Gln Glu Leu Asp Tyr Leu Thr Arg His Tyr
1               5                   10                  15

Leu

```
<210> SEQ ID NO 30
<211> LENGTH: 17
<212> TYPE: PRT
<213> ORGANISM: Staphylococcus aureus

<400> SEQUENCE: 30
```

Lys Lys Ser Val Thr Ala Gln Glu Leu Asp Ile Lys Ala Arg Asn Phe
1               5                   10                  15

Leu

```
<210> SEQ ID NO 31
<211> LENGTH: 17
<212> TYPE: PRT
<213> ORGANISM: Staphylococcus aureus

<400> SEQUENCE: 31
```

Lys Lys Ser Val Thr Ala Gln Glu Leu Asp Ile Lys Ala Arg Asn Phe
1               5                   10                  15

Leu

```
<210> SEQ ID NO 32
<211> LENGTH: 17
<212> TYPE: PRT
<213> ORGANISM: Staphylococcus aureus

<400> SEQUENCE: 32
```

Lys Lys Ser Val Thr Ala Gln Glu Leu Asp Ile Lys Ala Arg Asn Phe
1               5                   10                  15

Leu

```
<210> SEQ ID NO 33
<211> LENGTH: 17
<212> TYPE: PRT
<213> ORGANISM: Staphylococcus aureus

<400> SEQUENCE: 33
```

Lys Lys Asn Val Thr Val Gln Glu Leu Asp Ala Gln Ala Arg Arg Tyr
1               5                   10                  15

Leu

```
<210> SEQ ID NO 34
<211> LENGTH: 17
<212> TYPE: PRT
<213> ORGANISM: Staphylococcus aureus

<400> SEQUENCE: 34
```

Lys Lys Glu Val Thr Val Gln Glu Leu Asp Leu Gln Ala Arg His Tyr
1               5                   10                  15

Leu

```
<210> SEQ ID NO 35
<211> LENGTH: 17
<212> TYPE: PRT
<213> ORGANISM: Streptococcus pyrogenes

<400> SEQUENCE: 35

Lys Lys Met Val Thr Ala Gln Glu Leu Asp Tyr Lys Val Arg Lys Tyr
1               5                   10                  15

Leu

<210> SEQ ID NO 36
<211> LENGTH: 17
<212> TYPE: PRT
<213> ORGANISM: Streptococcus pyrogenes

<400> SEQUENCE: 36

Lys Asp Ile Val Thr Phe Gln Glu Ile Asp Phe Lys Ile Arg Lys Tyr
1               5                   10                  15

Leu

<210> SEQ ID NO 37
<211> LENGTH: 5
<212> TYPE: PRT
<213> ORGANISM: Staphylococcus aureus

<400> SEQUENCE: 37

Lys Lys Gln Leu Ile
1               5

<210> SEQ ID NO 38
<211> LENGTH: 9
<212> TYPE: PRT
<213> ORGANISM: Staphylococcus aureus

<400> SEQUENCE: 38

Leu Asp Phe Glu Ile Arg His Gln Leu
1               5

<210> SEQ ID NO 39
<211> LENGTH: 12
<212> TYPE: PRT
<213> ORGANISM: Staphylococcus aureus

<400> SEQUENCE: 39

Cys Met Tyr Gly Gly Val Ile Leu His Asp Asn Asn
1               5                   10

<210> SEQ ID NO 40
<211> LENGTH: 12
<212> TYPE: PRT
<213> ORGANISM: Staphylococcus aureus

<400> SEQUENCE: 40

Cys Met Tyr Gly Gly Val Thr Glu His Asn Gly Asn
1               5                   10

<210> SEQ ID NO 41
<211> LENGTH: 12
<212> TYPE: PRT
<213> ORGANISM: Staphylococcus aureus

<400> SEQUENCE: 41
```

```
Cys Met Tyr Gly Gly Ile Thr Lys His Glu Gly Asn
1               5                   10
```

<210> SEQ ID NO 42
<211> LENGTH: 12
<212> TYPE: PRT
<213> ORGANISM: Staphylococcus aureus

<400> SEQUENCE: 42

```
Cys Met Tyr Gly Gly Ile Thr Lys His Glu Gly Asn
1               5                   10
```

<210> SEQ ID NO 43
<211> LENGTH: 12
<212> TYPE: PRT
<213> ORGANISM: Staphylococcus aureus

<400> SEQUENCE: 43

```
Cys Met Tyr Gly Gly Ile Thr Lys His Glu Gly Asn
1               5                   10
```

<210> SEQ ID NO 44
<211> LENGTH: 12
<212> TYPE: PRT
<213> ORGANISM: Staphylococcus aureus

<400> SEQUENCE: 44

```
Cys Thr Tyr Gly Gly Val Thr Pro His Glu Gly Asn
1               5                   10
```

<210> SEQ ID NO 45
<211> LENGTH: 12
<212> TYPE: PRT
<213> ORGANISM: Staphylococcus aureus

<400> SEQUENCE: 45

```
Cys Met Tyr Gly Gly Val Thr Leu His Asp Asn Asn
1               5                   10
```

<210> SEQ ID NO 46
<211> LENGTH: 12
<212> TYPE: PRT
<213> ORGANISM: Streptococcus pyrogenes

<400> SEQUENCE: 46

```
Cys Ile Tyr Gly Gly Val Thr Asn His Glu Gly Asn
1               5                   10
```

<210> SEQ ID NO 47
<211> LENGTH: 12
<212> TYPE: PRT
<213> ORGANISM: Streptococcus pyrogenes

<400> SEQUENCE: 47

```
Tyr Ile Tyr Gly Gly Ile Thr Pro Ala Gln Asn Asn
1               5                   10
```

<210> SEQ ID NO 48
<211> LENGTH: 12
<212> TYPE: PRT
<213> ORGANISM: Staphylococcus aureus

<400> SEQUENCE: 48

```
Phe Gln Ile Ser Gly Val Thr Asn Thr Glu Lys Leu
1               5                   10
```

<210> SEQ ID NO 49
<211> LENGTH: 14
<212> TYPE: PRT
<213> ORGANISM: Staphylococcus aureus

<400> SEQUENCE: 49

Leu Leu Arg Ile Tyr Arg Asp Asn Lys Thr Ile Asn Ser Glu
1               5                   10

<210> SEQ ID NO 50
<211> LENGTH: 14
<212> TYPE: PRT
<213> ORGANISM: Staphylococcus aureus

<400> SEQUENCE: 50

Tyr Leu Met Met Tyr Asn Asp Asn Lys Met Val Asp Ser Lys
1               5                   10

<210> SEQ ID NO 51
<211> LENGTH: 14
<212> TYPE: PRT
<213> ORGANISM: Staphylococcus aureus

<400> SEQUENCE: 51

Tyr Leu Met Met Tyr Asn Asp Asn Lys Thr Val Asp Ser Lys
1               5                   10

<210> SEQ ID NO 52
<211> LENGTH: 14
<212> TYPE: PRT
<213> ORGANISM: Staphylococcus aureus

<400> SEQUENCE: 52

Tyr Leu Met Met Tyr Asn Asp Asn Lys Thr Val Asp Ser Lys
1               5                   10

<210> SEQ ID NO 53
<211> LENGTH: 14
<212> TYPE: PRT
<213> ORGANISM: Staphylococcus aureus

<400> SEQUENCE: 53

Tyr Leu Met Ile Tyr Lys Asp Asn Lys Met Val Asp Ser Lys
1               5                   10

<210> SEQ ID NO 54
<211> LENGTH: 14
<212> TYPE: PRT
<213> ORGANISM: Staphylococcus aureus

<400> SEQUENCE: 54

Gln Leu Arg Ile Tyr Ser Asp Asn Lys Thr Leu Ser Thr Glu
1               5                   10

<210> SEQ ID NO 55
<211> LENGTH: 14
<212> TYPE: PRT
<213> ORGANISM: Staphylococcus aureus

<400> SEQUENCE: 55

Leu Leu Arg Ile Tyr Arg Asp Asn Lys Thr Ile Asn Ser Glu
1               5                   10

-continued

<210> SEQ ID NO 56
<211> LENGTH: 14
<212> TYPE: PRT
<213> ORGANISM: Streptococcus pyrogenes

<400> SEQUENCE: 56

Tyr Leu Met Ile Tyr Lys Asp Met Glu Thr Leu Asp Ser Asn
1               5                   10

<210> SEQ ID NO 57
<211> LENGTH: 14
<212> TYPE: PRT
<213> ORGANISM: Streptococcus pyrogenes

<400> SEQUENCE: 57

Ile Phe Ala Lys Tyr Lys Asp Asn Arg Ile Ile Asn Met Lys
1               5                   10

<210> SEQ ID NO 58
<211> LENGTH: 14
<212> TYPE: PRT
<213> ORGANISM: Staphylococcus aureus

<400> SEQUENCE: 58

Pro Pro Ile Asn Ile Asp Glu Ile Lys Thr Ile Glu Ala Glu
1               5                   10

<210> SEQ ID NO 59
<211> LENGTH: 54
<212> TYPE: DNA
<213> ORGANISM: Staphylococcus aureus

<400> SEQUENCE: 59
tgctattttt catccaaaga taatgtaggt aaagttacag gtggcaaaac ttgt        54

<210> SEQ ID NO 60
<211> LENGTH: 18
<212> TYPE: PRT
<213> ORGANISM: Staphylococcus aureus

<400> SEQUENCE: 60

Cys Tyr Phe Ser Ser Lys Asp Asn Val Gly Lys Val Thr Gly Gly Lys
1               5                   10                  15

Thr Cys

<210> SEQ ID NO 61
<211> LENGTH: 42
<212> TYPE: DNA
<213> ORGANISM: Artificial Sequence
<220> FEATURE:
<223> OTHER INFORMATION: Synthetic

<400> SEQUENCE: 61
tgctattttt catccaaaga taatgcaggt ggcaaaactt gt        42

<210> SEQ ID NO 62
<211> LENGTH: 14
<212> TYPE: PRT
<213> ORGANISM: Artificial Sequence
<220> FEATURE:
<223> OTHER INFORMATION: Synthetic -continued

```
<400> SEQUENCE: 62

Cys Tyr Phe Ser Ser Lys Asp Asn Ala Gly Gly Lys Thr Cys
1               5                   10

<210> SEQ ID NO 63
<211> LENGTH: 27
<212> TYPE: DNA
<213> ORGANISM: Artificial Sequence
<220> FEATURE:
<223> OTHER INFORMATION: Synthetic

<400> SEQUENCE: 63
tgctattttt catccggcaa aacttgt                                           27

<210> SEQ ID NO 64
<211> LENGTH: 9
<212> TYPE: PRT
<213> ORGANISM: Artificial Sequence
<220> FEATURE:
<223> OTHER INFORMATION: Synthetic

<400> SEQUENCE: 64

Cys Tyr Phe Ser Ser Gly Lys Thr Cys
1               5

<210> SEQ ID NO 65
<211> LENGTH: 18
<212> TYPE: DNA
<213> ORGANISM: Artificial Sequence
<220> FEATURE:
<223> OTHER INFORMATION: Synthetic

<400> SEQUENCE: 65
tgctgtggca aaacttgt                                                     18

<210> SEQ ID NO 66
<211> LENGTH: 6
<212> TYPE: PRT
<213> ORGANISM: Artificial Sequence
<220> FEATURE:
<223> OTHER INFORMATION: Synthetic

<400> SEQUENCE: 66

Cys Cys Gly Lys Thr Cys
1               5
```